United States Patent
Eaton

(10) Patent No.: US 6,245,960 B1
(45) Date of Patent: *Jun. 12, 2001

(54) INHERENT HEALING ACCELERATOR

(75) Inventor: L. Daniel Eaton, Little Rock, AR (US)

(73) Assignee: Board of Trustees of the University of Arkansas, Little Rock, AR (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/311,041

(22) Filed: May 13, 1999

(51) Int. Cl.[7] .................................... A61F 13/00
(52) U.S. Cl. .................. 602/47; 602/41; 602/42; 602/43; 602/44; 602/45; 602/46
(58) Field of Search .......................... 602/41–47

(56) References Cited

U.S. PATENT DOCUMENTS

| | | |
|---|---|---|
| 2,693,438 | 11/1954 | Ward . |
| 3,366,975 | 2/1968 | Pangman . |
| 3,543,750 * | 12/1970 | Meizanis . |
| 3,803,300 | 4/1974 | Pospischil . |
| 3,867,520 | 2/1975 | Mori et al. . |
| 3,897,376 | 7/1975 | Lampe . |
| 3,925,277 | 12/1975 | Lampe . |
| 4,399,123 * | 8/1983 | Oliver et al. . |
| 4,725,279 | 2/1988 | Woodroof . |
| 4,731,081 | 3/1988 | Tiffany et al. . |
| 4,838,253 | 6/1989 | Brassington et al. . |
| 4,867,150 * | 9/1989 | Gilbert . |
| 4,871,366 * | 10/1989 | Von Recum et al. . |
| 4,995,882 | 2/1991 | Destouet et al. . |
| 5,196,190 | 3/1993 | Nangia et al. . |
| 5,282,856 | 2/1994 | Ledergerber . |
| 5,358,521 | 10/1994 | Shane . |
| 5,376,323 | 12/1994 | Eaton . |
| 5,395,305 | 3/1995 | Koide et al. . |
| 5,496,367 | 3/1996 | Fisher . |
| 5,496,370 | 3/1996 | Hamas . |
| 5,635,201 * | 6/1997 | Fabo . |
| 5,656,588 * | 8/1997 | Zaloga et al. . |
| 5,895,656 * | 4/1999 | Hirshowitz et al. . |

* cited by examiner

Primary Examiner—Michael A. Brown
Assistant Examiner—Lalita M. Hamilton
(74) Attorney, Agent, or Firm—Ray F. Cox, Jr.

(57) ABSTRACT

A process and device for improved healing of large avulsed or burned tissue which prevents excessive cicatricial, keloid or fibromatoid formation, reduces fluid loss, and increases protection from infection by employing an elastomer matrix; i.e., a thin sheet of elastomer with a plurality of fenestrations, placed on the wound and a bath of oil to cover the matrix. The oil bath is provided by a flexible sealed capsule of thin silicone elastomer, preferably filled with soybean oil that percolates through the walls of the capsule. Enhanced granulation tissue formation is promoted by encapsulation of the wound with the matrix. Granulation tissue engulfs the matrix while the matrix integrity and elastic rigidity acts to reduce scarring. The barrier of the sterile soybean oil bath and the barrier of the elastomer matrix improve antisepsis and acts to reduce loss of body fluids. The matrix encourages the generation of granulation tissue since the matrix appears to the body as a foreign object that the body tries to reject.

22 Claims, 5 Drawing Sheets

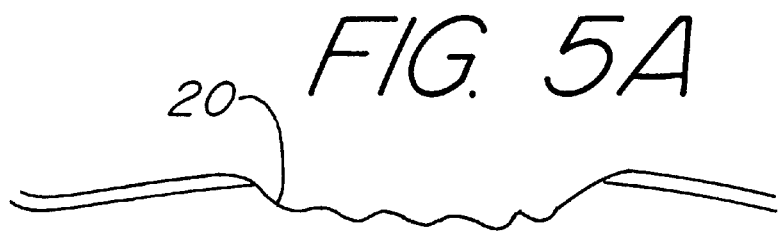
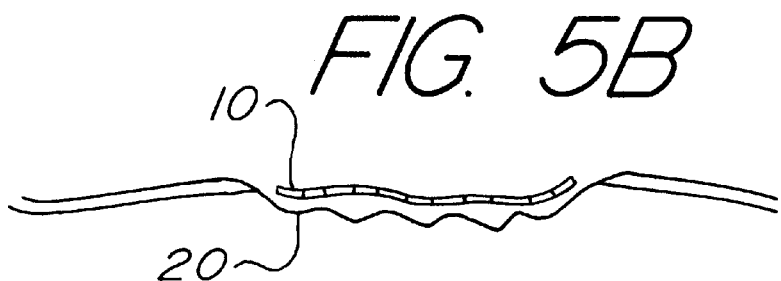
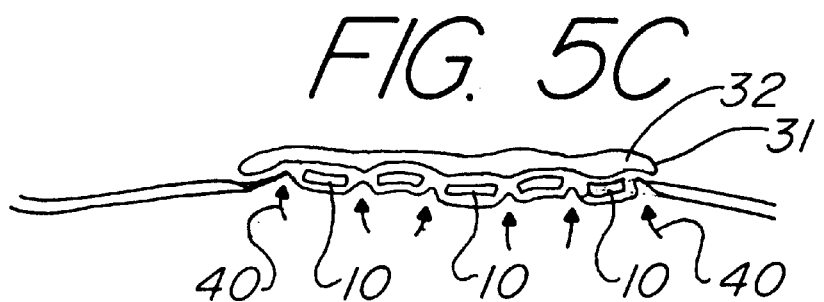
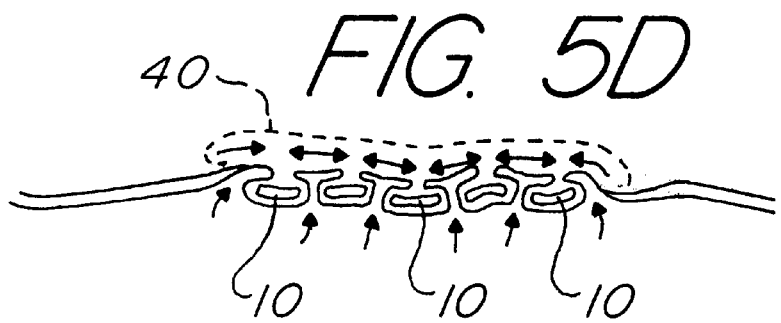
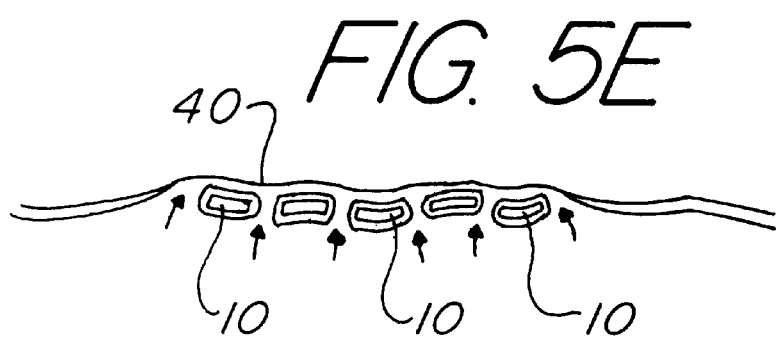

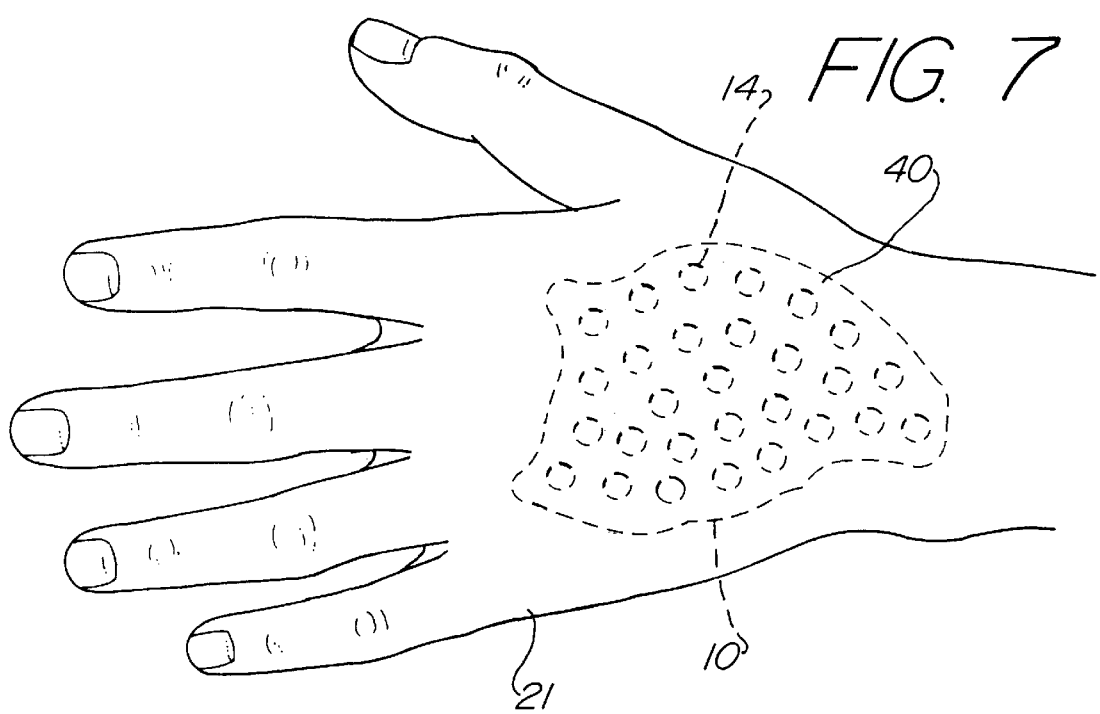

INHERENT HEALING ACCELERATOR

BACKGROUND OF THE INVENTION

The present invention relates to materials and methods for assisting in the healing of avulsed, burned, or ablative wounds, and in particular, to materials and methods which prevent excessive cicatricial, keloid, or fibromatoid formation, reduce fluid loss and provide protection from infection.

The treatment of open wounds has been hampered by a number of factors. It is desirable, for example, that such open wounds be protected against both infection and fluid loss by covering the wounds with a dressing. Dressings of fibrous material may actually interfere with the healing of the wound by becoming incorporated with the scab or granulation tissue and thus necessitating later surgical removal from the wound. Dressings of synthetic film have been employed but may also interfere with the healing of the wound by causing excessive accumulation of fluid beneath the dressing and may further interfere with healing since the body may tend to reject the synthetic material.

An additional problem with the healing of a large area wound is that of excessive scarring during the healing process. Various attempts have been made to address some or all of these problems.

U.S. Pat. No. 4,725,279 discloses a bio-and blood compatible material for a thermal burn dressing. The material is a composite comprising a thin film of thermoplastic material, such as Silastic ® (Dow Corning), a knitted or woven layer, and a bonded layer of biological molecules to render the material bio-and blood compatible. It is disclosed that the material has a vapor transmission rate comparable to the human skin and that it is desirable that the wound site be closed as occlusively as possible without allowing liquid to accumulate between the wound surface and the material of this invention. To avoid this effect a variant embodiment provides for "pinholes" in the material such that the material remains 98% or better occlusive.

U.S. Pat. No. 4,838,253 discloses a liquid permeable dressing comprising one or more sheets of apertured material, such as cotton gauze, coated with a tacky silicone gel or a non-tacky silicone elastomer.

U.S. Pat. No. 5,395,305 discloses a wound-covering material comprising two layers: a first support layer which is in contact with the wound and which contains a water repelling substance and a second moisture permeation controlling layer which may be formed from steam permeable resin films made of silicone or polyurethane elastomers.

U.S. Pat. No. 2,693,438 discloses a non-adherent pliable film for a surgical dressing. The dressing film is formed from water-soluble polyvinyl alcohol mixed with a plasticizing agent and water. The film may be reinforced by embedding a textile material in the outer layer. It is specifically noted that the film will not irritate the lesion or become incorporated in the scab or granulation tissue formed therein.

U.S. Pat. No. 5,196,190 discloses a membrane suitable for wound dressing comprising a natural or synthetic polymer, a non-gellable polysaccharide and a cross-linking agent. The membranes may also contain water-loss control agents, emulsifying agents, plasticizers, or an internal reinforcing material.

U.S. Pat. No. 3,803,300 discloses an ointment foil for application to skin. The ointment foil is prepared by drying an oil-in-water emulsion of ointment ingredients to a moisture content of 1% to 15%.

U.S. Pat. No. 3,867,520 discloses a medicated polyamino acid film for occlusive dressing therapy.

The limitations of the prior art are overcome by the present invention as described below.

SUMMARY OF THE INVENTION

The present invention is a combination process and device for improved rapid safe healing of large areas of avulsed or burned tissue which prevents excessive cicatricial, keloid or fibromatoid formation, greatly reduces fluid loss, and increases protection from infection.

An elastomer matrix; i.e., a thin sheet of elastomer with a plurality of fenestrations, is placed on the wound and a bath of oil, preferably soybean oil, in turn covers the fenestrated elastomer matrix. The elastomer is preferably medical grade Silastic®, available from Dow Corning. The soybean oil bath is provided by a flexible sealed capsule of thin elastomer, preferably Silastic® filled with soybean oil. The soybean oil bath overlaps the wound margin periphera by one centimeter or more. The thin capsule walls allow the soybean oil to slowly percolate through the walls that are semi-permeable to the soybean oil.

Enhanced granulation tissue formation is promoted by encapsulation of the wound with the elastomer matrix. As healing proceeds, granulation tissue engulfs the elastomer matrix while the matrix integrity and flexible rigidity acts to prevent drawing of the tissue and thereby reduces scarring.

In addition to reduced skin tissue scarring and more rapid healing, the present invention has the advantage of improved antisepsis due both to the barrier of the sterile soybean oil bath and the barrier of the elastomer matrix. In the preferred embodiment, the matrix presents a barrier of approximately half of its area (the remaining area being the fenestrations which do not of course provide a barrier).

The combination of the elastomer matrix and the soybean oil bath also acts to reduce loss of body fluids, which is significant to large burn surface areas, while allowing the wound to be inspected and cleaned as necessary. The elastomer matrix encourages the generation of granulation tissue since the elastomer matrix appears to the body as a foreign object that the body tries to reject.

The present invention is applicable to large avulsed, burned, ablative or disfiguring traumatic wounds. The invention is also applicable to tissue augmentation for tissue volume loss; e.g., pseudotosis.

It is therefore an object of the present invention to provide for an elastomer matrix with fenestrations allowing the penetration of granulation tissue through the fenestrations so as to cover the matrix as the wound heals.

It is a further object of the present invention to provide for the addition of an oil bath to further protect the wound during the healing process.

These and other objects and advantages of the present invention will be apparent from a consideration of the following detailed description of the preferred embodiments in conjunction with the appended drawings as described following.

BRIEF DESCRIPTION OF THE DRAWINGS

FIGS. 5A–5E are sectional views through the open wound of FIGS. 1–4 showing the open wound alone (FIG. 5A), the open wound covered by the fenestrated elastomer matrix (FIG. 5B), the open wound covered by the oil bath and the beginning of the formation of granulation tissue through the fenestrations (FIG. 5C), the wound showing the growth of granulation tissue over the upper surface of the fenestrated elastomer matrix and under the oil bath (FIG. 5D), and the complete overgrowth of granulation tissue over the fenestrated elastomer matrix (FIG. 5E).

FIG. 7 is a perspective view of the healed wound showing the embedded fenestration elastomer matrix in shadow outline under the healed surface of the patient's hand.

DETAILED DESCRIPTION OF THE PREFERRED EMBODIMENTS

With reference to FIGS. 1–7, the preferred embodiments of the present invention may be described. The present invention is a combination process and device for improved rapid safe healing of large areas of avulsed or burned tissue which prevents excessive cicatricial, keloid or fibromatoid formation, greatly reduces fluid loss, and increases protection from infection.

Figure 1:
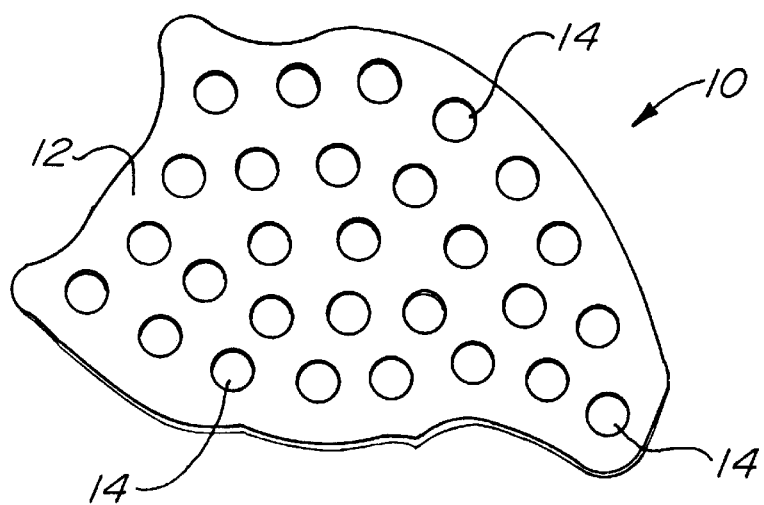
FIG. 1 is a perspective view of the fenestrated elastomer matrix of the present invention.

With reference to FIG. 1, an elastomer matrix 10 comprises a thin elastomer sheet 12 with a plurality of fenestrations 14. The elastomer should be flexible and yet sufficiently rigid to aid in minimizing scarring as described more fully below. The elastomer is preferably a silicone material. It has been found that medical grade Silastic®, available from Dow Corning, is acceptable for the practice of the present invention. Various techniques known in the art would be suitable for the manufacture of the elastomer matrix 10.

Figure 2:
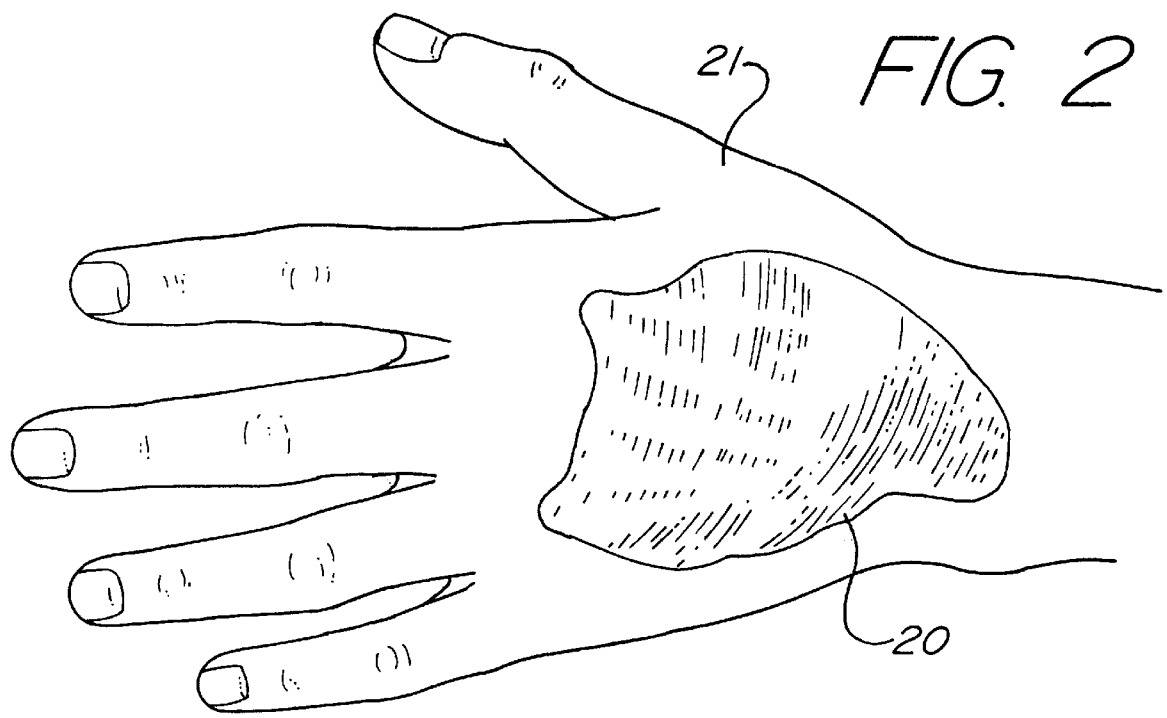
FIG. 2 is a perspective view of an open wound on the hand of a patient to be treated by the method and devices of the present invention.

The elastomer matrix 10 is employed directly as a dressing on an open wound 20 such as that illustrated in FIG. 2. The elastomer matrix 10 should be slightly smaller than the margins of the wound to allow granulation tissue to grow around the elastomer matrix 10. FIG. 2 is shown with the open wound 20 on the hand 21 of a patient, but this is merely by way of example and the present invention may be employed on all types and locations of open wounds. Open wounds due to ablative trauma or burns may be exceptionally difficult to heal, particularly in locations not well vascularized or subject to poor blood circulation. Major concerns are fluid loss and infection. The elastomer matrix 10 provides protection to the open wound 20, minimizing the chance of infection and fluid loss. In the preferred embodiment, the elastomer matrix 10 presents a barrier of approximately half of its surface area (the remaining surface area being the fenestrations 14 which do not of course provide a barrier). It is desirable that the elastomer matrix 10 provide a high degree of occlusion of the wound to minimize the chances of infection and to minimize fluid loss. It is necessary however that the fenestrations 14 be large enough so that the granulation tissue may grow completely over the elastomer matrix 10. It has been found to be preferable that the fenestrations 14 comprise 40–60% of the surface area of the elastomer matrix 10 and most preferably, around 50%. It has also been found to be desirable that the fenestrations 14 be 4–6 millimeters in maximum dimension, and preferably around 5 millimeters in maximum dimension, for the same reason. Smaller wounds require smaller size fenestrations 14 and larger wounds require larger fenestrations 14 to avoid excessive scarring.

Figure 3:
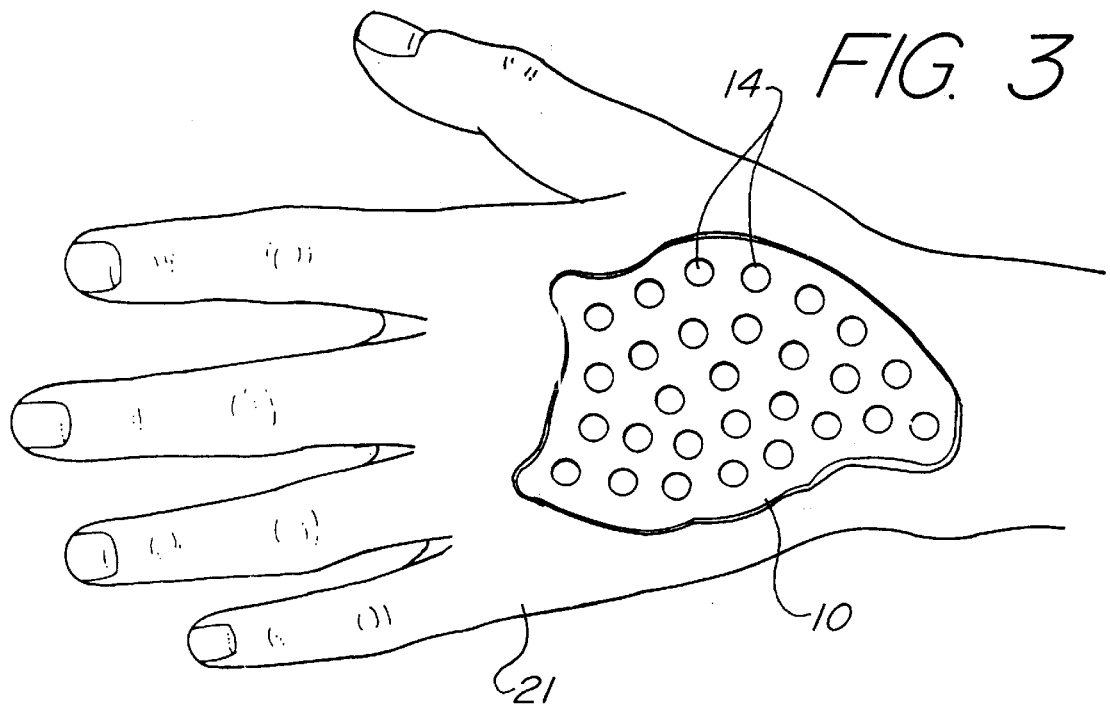
FIG. 3 is a perspective view of the open wound of FIG. 2 covered by the fenestrated elastomer matrix of FIG. 1.

The elastomer matrix 10 is placed on the open wound 20 as shown in FIG. 3 so as to cover the entire wound 20. As noted above, it is necessary for the matrix 10 to be smaller than the margins of the wound in order to allow the granulation tissue to grow completely around and over the matrix 10. The elastomer matrix 10 encourages the generation of granulation tissue since the elastomer matrix 10 appears to the body as a foreign object which the body tries to reject. Once the elastomer matrix 10 is placed on the open wound 20 enhanced granulation tissue formation begins as shown in FIGS. 5A–5E. As healing proceeds, granulation tissue 40 (indicated by the arrows in FIGS. 5C–5E) engulfs the elastomer matrix 10 while the matrix integrity and flexible rigidity acts to prevent the newly formed tissue from drawing and thus reduces scarring. The undesirable appearance of scar tissue is exacerbated by the puckering and wrinkling that occur as the tissue heals. In the present invention, the elastomer matrix 10 discourages the formation of excessive cicatricial, keloid, or fibromatoid formation. Unlike prior art dressings, the elastomer matrix 10 of the present invention is designed to remain in the healed wound 20 as shown by FIG. 7. In the prior art, dressings are changed regularly, often promoting scarring since the removal of dressings from a wound normally involves tearing the scab or granulation tissue already forming within the dressing or attached to the dressing.

Figure 4:
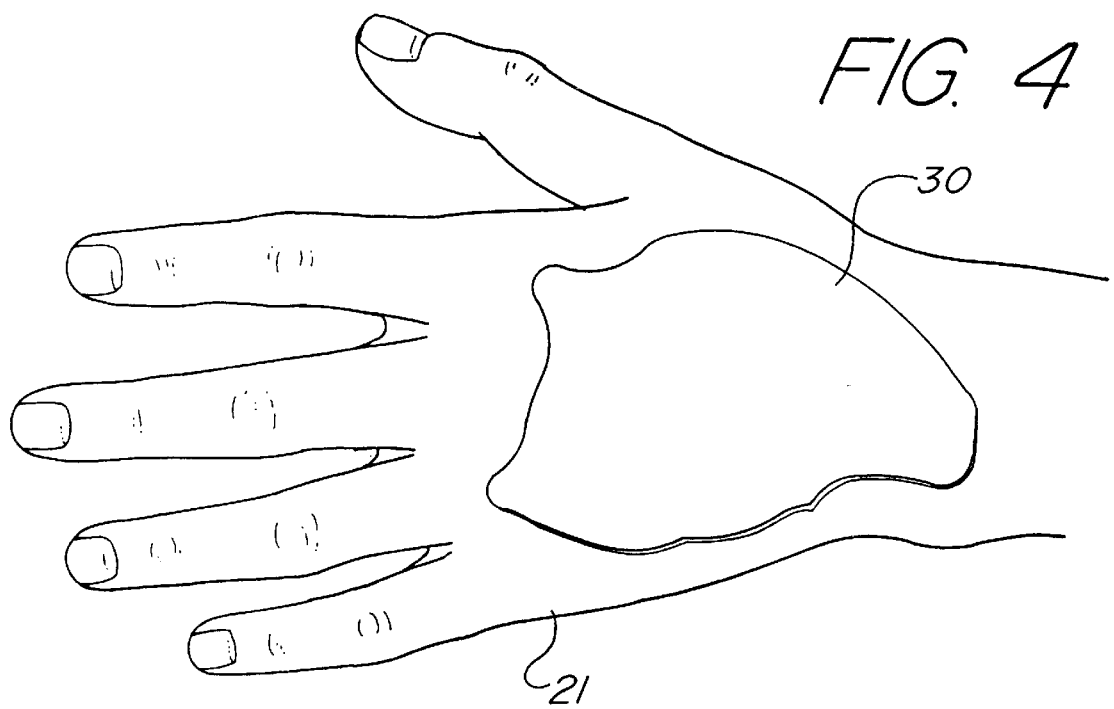
FIG. 4 is a perspective view of the open lesion of FIG. 2 covered by the oil bath.
Figure 6:
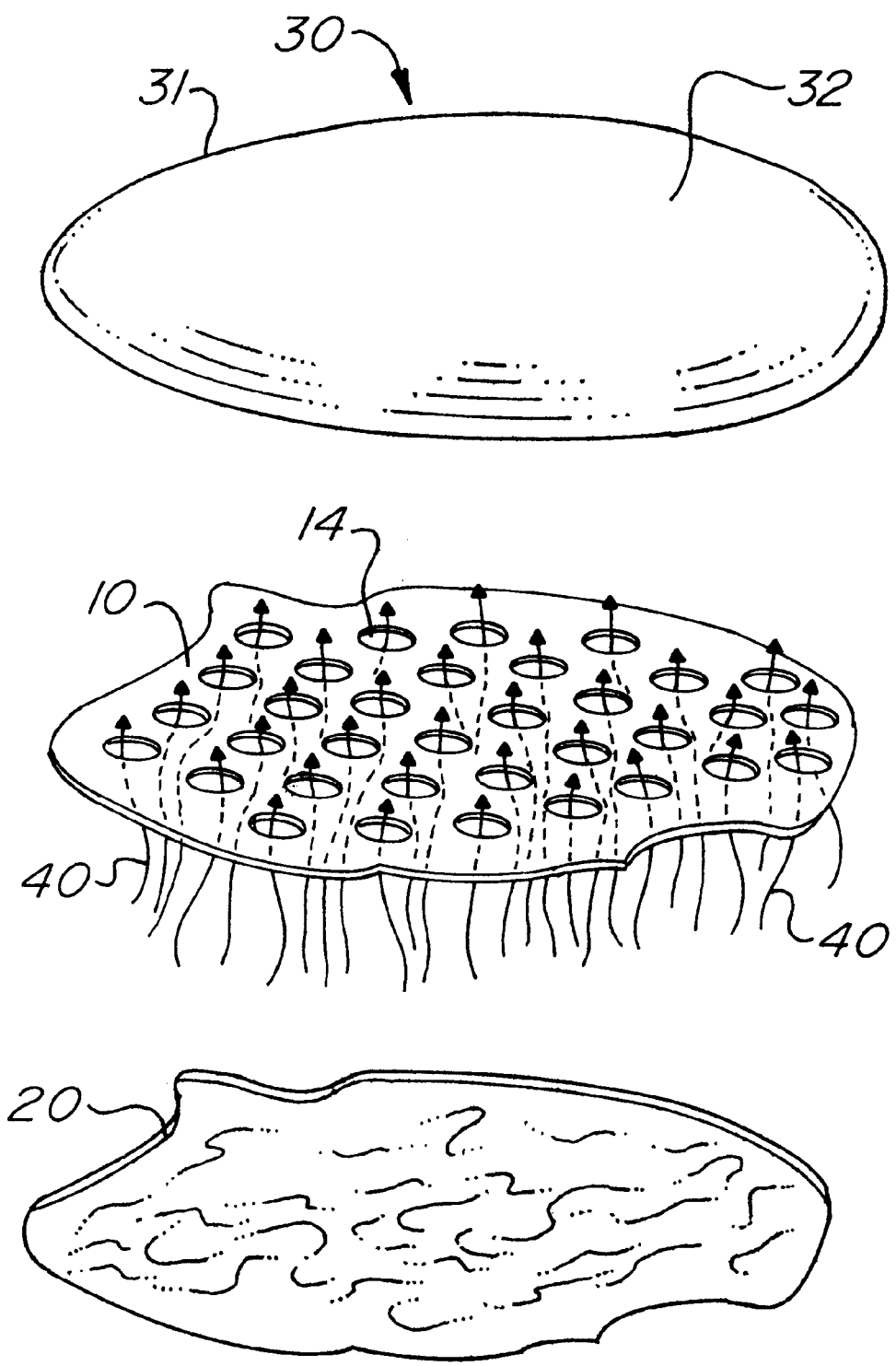
FIG. 6 is an exploded perspective view of the open lesion, fenestrated elastomer matrix, and oil bath.

To assist in the healing process and to provide an additional barrier to protect the open wound 20 during the healing process, an oil bath 30 is provided to cover the elastomer matrix 10 as shown in FIG. 4. The oil bath 30 comprises a flexible sealed thin elastomer capsule 31 filled with oil. The oil is preferably a triglyceride oil, such as soybean oil or rice oil. The capsule 31 is preferably made of silicone elastomer. It has been found that Silastic® is acceptable in the practice of the present invention. In the preferred embodiment the capsule 31 is filled with soybean oil. Soybean oil (trilipid Z5) is a natural triglyceride and has been used for 40 years as an I.M. drug carrier.

The oil bath 30 preferably overlaps the wound margin periphera by one centimeter or more. The thin walls of the capsule 31 allow the oil 32 to slowly percolate through the walls of the capsule 31, which are semi-permeable to the oil 32. It has been found that a thin capsule of medical grade Silastic® is adequately permeable to soybean oil. The combination of the elastomer matrix 10 and the oil bath 30 provide, in addition to reduced skin tissue scarring and more rapid healing, the advantage of improved antisepsis due both to the barrier of the sterile oil bath 30 and the barrier of the elastomer matrix 10. This combination of the elastomer matrix 10 and the oil bath 30 also acts to reduce loss of body fluids which is significant to large burn surface areas.

While the detailed description of the preferred embodiment of the present invention has been given with respect to large avulsed, burned, ablative or disfiguring traumatic wounds, the invention is also applicable to tissue augmentation for tissue volume loss; e.g., pseudotosis.

The present invention has been described with reference to certain preferred and alternative embodiments that are intended to be exemplary only and not limiting to the full scope of the present invention as set forth in the appended claims.

What is claimed is:

1. A dressing for open wounds, comprising an elastomer sheet having a plurality of fenestrations, wherein said fenestrations comprise openings penetrating through said elastomer sheet whereby granulation tissue may grow from the open wound through said fenestrations so as to substantially cover said elastomer sheet; wherein each of said fenestrations comprise a maximum dimension of around 4 millimeters to around 6 millimeters.

2. The dressing of claim 1 wherein each of said fenestrations comprise a maximum dimension of around 5 millimeters.

3. The dressing of claim 1 wherein said elastomer sheet comprises silicone elastomer.

4. The dressing of claim 1 wherein said fenestrations comprise around 40% to around 60% of the surface area of said elastomer sheet.

5. The dressing of claim 4 wherein said fenestrations comprise around 50% of the surface area of said elastomer sheet.

6. A composite dressing for open wounds, comprising an elastomer sheet having a plurality of fenestrations; and an oil bath, wherein said fenestrations comprise openings penetrating through said elastomer sheet whereby granulation tissue may grow from the open wound through said fenestrations so as to substantially cover said elastomer sheet; wherein said oil bath comprises a capsule containing a triglyceride oil, said capsule having walls permeable to said triglyceride oil.

7. The composite dressing of claim 6 wherein said walls of said capsule comprise silicone elastomer.

8. The composite dressing of claim 7 wherein said triglyceride oil comprises soybean oil.

9. The composite dressing of claim 6 wherein said fenestrations comprise around 40% to around 60% of the surface area of said elastomer sheet.

10. The composite dressing of claim 9 wherein said fenestrations comprise around 50% of the surface area of the elastomer sheet.

11. The composite dressing of claim 6 wherein each of said fenestrations comprise a maximum dimension of around 4 millimeters to around 6 millimeters.

12. The composite dressing of claim 6 wherein each of said fenestrations comprise a maximum dimension of around 5 millimeters.

13. The composite dressing of claim 6 wherein said elastomer sheet comprises silicone elastomer.

14. A method of promoting healing of open wounds with reduced scarring, comprising the steps of:
   covering said open wound with a composite dressing comprising an elastomer sheet having a plurality of fenestrations, said fenestrations comprising openings penetrating through said elastomer sheet, and an oil bath; and
   allowing granulation tissue to grow through said fenestrations until said elastomer sheet is substantially covered by said granulation tissue.

15. The method of claim 14 wherein said oil bath comprises a capsule containing a triglyceride oil, said capsule having walls permeable to said triglyceride oil.

16. The method of claim 14 wherein said walls of said capsule comprise silicone elastomer.

17. The method of claim 16 wherein said triglyceride oil comprises soybean oil.

18. The method of claim 16 wherein said fenestrations comprise around 40% to around 60% of the surface area of the elastomer sheet.

19. The method of claim 18 wherein said fenestrations comprise around 50% of the surface area of the elastomer sheet.

20. The method of claim 14 wherein each of said fenestrations comprise a maximum dimension of around 4 millimeters to around 6 millimeters.

21. The composite dressing of claim 20 wherein each of said fenestrations comprise a maximum dimension of around 5 millimeters.

22. The method of claim 14 wherein said elastomer sheet comprises silicone elastomer.

* * * * *